(12) United States Patent
Martin

(10) Patent No.: US 8,088,829 B2
(45) Date of Patent: Jan. 3, 2012

(54) BIOCIDAL ALDEHYDE COMPOSITION

(76) Inventor: Howard Martin, Rockville, MD (US)

( * ) Notice: Subject to any disclaimer, the term of this patent is extended or adjusted under 35 U.S.C. 154(b) by 295 days.

(21) Appl. No.: 12/584,648

(22) Filed: Sep. 9, 2009

(65) Prior Publication Data

US 2011/0059027 A1 Mar. 10, 2011

(51) Int. Cl.
*A01N 35/00* (2006.01)
*A61K 31/11* (2006.01)
(52) U.S. Cl. .......... 514/699; 514/698; 514/693; 514/705
(58) Field of Classification Search .................. None
See application file for complete search history.

(56) References Cited

U.S. PATENT DOCUMENTS

| | | | |
|---|---|---|---|
| 4,851,449 A | 7/1989 | Bruckner et al. | |
| 4,983,635 A | 1/1991 | Martin | |
| 5,252,606 A * | 10/1993 | Martin | 514/574 |
| 5,284,875 A | 2/1994 | Martin | |
| 6,627,178 B1 * | 9/2003 | Cawthon | 424/45 |

FOREIGN PATENT DOCUMENTS

| | | | | |
|---|---|---|---|---|
| CN | 1613308 A | * | 5/2005 | |
| FR | 2743982 A1 | * | 8/1997 | |
| GB | 2355408 A | * | 4/2001 | |
| JP | 11140010 A | * | 5/1999 | |

OTHER PUBLICATIONS

Shackelford et al., Use of a new alginate film test to study the bactericidal efficacy of the high-level disinfectant ortho-phthalaldehyde, *Journal of Antimicrobial Chemotherapy*, 57(2) :335-338 (2006).

* cited by examiner

*Primary Examiner* — Johann Richter
*Assistant Examiner* — Daniel L Branson
(74) *Attorney, Agent, or Firm* — Ober, Kaler, Grimes & Shriver; Royal W. Craig

(57) ABSTRACT

A novel combination of OPA, a surfactant, and alcohol. The surfactant is preferably a dual chain quaternary ammonium compound consisting of a mixture of alkyl dimethylbenzylammonium chlorides and alkyl dimethylethylbenzylammonium, that absorbs onto a surface and alters the free energy of that surface. The alcohol is preferably isopropyl alcohol. The OPA is the dialdehyde $C_6H_4(CHO)_2$, which produces an inherent bacteriostatic effect and lowers surface tension and thus aids in the spread of the dual quat on the biofilm covered surface where it is readily absorbed by the negative surfaces of proteins and bacteria. It thus serves as a binding agent between the dual quat and the application surface. This multi purpose component helps create the unique aspect of the formulation. The three foregoing constituents are combined in preferred concentrations within acceptable ranges to provide a synergistic formulation that combines biocidal molecules in a biological chemical system that actively transports itself into the cells, through biofilm and cell wall/membranes, thereby overcoming penetration restraints to improve kill and kill time, without the need for activation or any time or temperature control. This is an effective example of synergistic complementarity.

9 Claims, No Drawings

BIOCIDAL ALDEHYDE COMPOSITION

BACKGROUND OF THE INVENTION

1. Field of the Invention

The present invention relates to chemical disinfection and sanitizing and, more particularly, to an improved biocidal aldehyde composition for surface disinfection/sterilization.

2. Description of the Background

The purpose of disinfection is to reduce microbial contamination to an innocuous level. There is a widespread need for effective microbials in the healthcare industry (e.g., medical instrument sterilization). There are also myriad existing compositions that purport to solve the need, but in reality the results are mixed. Moreover, certain chemicals are inappropriate for certain situations. For example, Iodine is one of the most effective antimicrobial agents known. It is essentially bactericidal, and in diluted form the bacteriostatic and bactericidal action is practically identical. Iodine is active against a broad series of organisms including TB, pathogenic fungi, and viruses of both lipophilic and hydrophilic types. Although effective as an antiseptic wash and irrigant over a wide pH range it is best at an acid pH.

There are several combinations of quaternary ammonium compounds used for biocidal purposes, but they are application specific. Quaternary ammonium compounds are inhibitory to vegetative organisms and fungi but are not tuberculocidal or sporicidal. Quaternary ammonium compounds cannot generally be provided in concentrate form because they are inactivated by hard water (water with more than 400 ppm of carbonates). They also present an environmental problem. Certain dual quaternary ammonium compounds have improved biocidal activity, stronger detergency and a low level of toxicity, but they still have not solved the hard water problem that reduces or inhibits their activity, nor the environmental problems. For example, U.S. Pat. No. 4,983,635 issued Jan. 8, 1991, and U.S. Pat. No. 5,284,875 issued Feb. 8, 1994, solved the hard water problem and improved but did not effectively solve the biocidal activity. Moreover, due to the addition of phenolics this prior art increased the toxicity problem.

Glutaraldehyde is still currently the most important high level disinfectant/sterilant in health care usage. However, its use over the years has shown it to be erratic, failing in certain tuberculosis (TB) tests. Moreover, it requires burdensome time/temperature control (residence time of 45-90 minutes for disinfection, and controlled temperature of from 20 C to 25-30 C). Consequently, glutaraldehyde has very limited usage in clinical settings where temperatures are between 20-22 degrees C. If the user fails to warm the solution or its labels do not indicate that this warming should accompany its use, there is risk of ineffectiveness. The most popular commercial product Cidex™ requires activation and dating to make it useful. Thus, proper usage entails a three step procedure and meticulous record-keeping regarding date of activation.

A different aldehyde, orthophthaldehyde (OPA), has now come into use. Johnson and Johnson developed an original formulation in the late 1980s described in U.S. Pat. No. 4,851,449 and in subsequent continuation in part application(s). This OPA has been approved by the FDA as a high level disinfectant with a twelve minute disinfection time at 20-22 degrees C. Its sterilization time is listed between 24-32 hours. OPA interacts with amino acids and proteins of microorganisms. OPA is lipophilic which improves its uptake in the cell walls. Thus, OPA has been shown to be more penetrating than glutaraldehyde. The J&J OPA concentration is 0.55% by weight at a pH 3-9. It has been shown to be effective in a purely aqueous immersion solution. Metrex Research Corp. continues to sell a modified formulation referred to as OPA+, with an increased OPA concentration of 0.6% (0.05% more OPA), plus buffers, a corrosion inhibitor, and a chelating agent. In essence the formula is the same as the J&J product, with no faster kill time, but claims of 60% more treatment. However, if one looks at the mechanism by which OPA works it becomes biologically clear where the weaknesses lie. OPA is an aromatic dialdehyde. The severe test for cidal effectiveness are gram negative bacteria, mycobacteria and spore-coated organisms. OPA is not completely effective in clinical use at its concentration of 0.5% and pH 6.5. Failures occur and have been reported in literature surveys. The benzene ring of OPA is a planar, rigid structure. Therefore, OPA has no flexibility as a result of steric hinderance. In addition, OPA only reacts with primary amines. OPA is bactericidal at low concentrations to staphylococci and gram-bacteria. The poor sporicidal activity is due to low concentration and low pH. It has been noted that if the temperature is raised from the normal 20 degrees C. to 30 degrees it improves. However, this is impractical. Regarding mycobacteria, a similar problem is present. The lipophilic aromatic component of OPA does not reliably penetrate the lipid-rich cell wall of mycobacteria and gram (−) bacteria. Indeed, subsequent studies show that OPA exhibits selective bactericidal activity, good against *P. aeruginosa*, limited activity against mycobacterial strains. Shackelford et al., *Use of a New Alginate Film Test To Study The Bactericidal Efficacy Of The High-Level Disinfectant Ortho-Phthalaldehyde*, Journal of Antimicrobial Chemotherapy, 57(2):335-338 (2006).

What is needed is a simple one-step formulation for more effective disinfection/sterilization of health care instruments and other surfaces.

SUMMARY OF THE INVENTION

It is, therefore, an object of the present innovation to provide a novel strategy for potentiating and improving the cidal effectiveness of orthophthalaldehyde by a synergistic formulation that combines cidal molecules with a biological chemical system that actively transports itself into the cells, through the biofilm and cell wall/membranes, thereby overcoming penetration restraints.

It is another object to improve cidal effectiveness against a broader range of refractory microorganisms within ecological and environmentally acceptable parameters, essentially yielding a green biocide.

In one embodiment designed for healthcare, these and other objects are accomplished by a novel combination of OPA, a surfactant, and alcohol. The surfactant is preferably a dual chain quaternary ammonium compound comprising a mixture of alkyl dimethyl-benzylammonium chlorides and alkyl dimethylethyl-benzylammonium, that absorbs onto a surface and alters the free energy of that surface. The alcohol is preferably isopropyl alcohol. The OPA is the dialdehyde $C_6H_4(CHO)_2$, which produces an inherent bacteriostatic effect and lowers surface tension and thus aids in the spread of the dual quat on the biofilm covered surface where it is readily absorbed by the negative surfaces of proteins and bacteria. It thus serves as a binding agent between the dual quat and the application surface. This multi-purpose component helps create the unique aspect of the formulation. The three foregoing constituents are combined in preferred concentrations within acceptable ranges to provide a synergistic formulation that combines cidal molecules with a biological chemical system that actively transports itself into the cells, through the biofilm and cell wall/membranes, thereby overcoming penetration restraints to improve kill and kill time, without the need for activation or any time or temperature control.

Other objects, features, and advantages of the present invention will become more apparent from the following detailed description of the preferred embodiments and certain modifications thereof.

DETAILED DESCRIPTION OF THE PREFERRED EMBODIMENT

The present invention is an OPA-based solution with a synergistic complementarity of constituents that combine to improve the cidal effectiveness of the orthophthalaldehyde through a biological chemical system to provide improved results. The present invention allows a one-step formulation for disinfection/sterilization of health care instruments and surfaces by application as an immersion solution, wipe or spray, or as an aqueous solution. The unique chemo-biological formulation described herein improves the cidal effectiveness OPA by the addition of certain long chain polymer cationic surfactants, the combination creating a synergistic and unexpected improvement in biocidal effectiveness resulting in faster kill time.

In the healthcare context, the core constituents of the inventive formulation are a novel combination of OPA, a surfactant, and alcohol. The surfactant (i.e. surface active agent) is a substance that when present in low concentration in solution has the property of absorbing on to a surface and altering the free energy of that surface. The preferred surfactant is a dual chain quaternary ammonium compound comprising of a mixture of alkyl dimethyl-benzylammonium chlorides and alkyl dimethylethylbenzylammonium.

The alcohol is preferably isopropyl alcohol.

The three foregoing constituents are combined in the following preferred concentrations within acceptable ranges, the balance being primarily water, plus inert additives as desired including Trienthanol Amine, Glycol Ether, and Sulfonic Acid.

| Constituent | % by weight | Acceptable Range |
|---|---|---|
| OPA | 5% | 0.25-7% |
| Dual Chain Quat | .48% | .24-6% |
| Isopropyl Alcohol | 41.5% | 10-60% |
| Trienthanol amine | 0.5% | 0.25-2% |
| Glycol Ether | 4% | 2%-6% |
| Sulfonic Acid | 2% | 0.2-3% |

The preferred formula amount of constituents indicated above is best suited for clinical usage, and the amounts/concentrations may vary for other uses as described below.

The orthophthalaldehyde (OPA) is a chemical compound with the formula $C_6H_4(CHO)_2$. The molecule is a dialdehyde, consisting of two formyl (CHO) groups attached to adjacent carbon centers on a benzene ring. It is a pale yellow solid and is readily commercially available. The OPA, in addition to its inherent bacteriostatic effect (see Grump, W. "Disinfectants and Antiseptics" in Kirk-Othmer, Encyclopedia of Chemical Technology, vol. 7, 3rd ed., 1979) lowers surface tension and thus aids in the spread of the dual quat on the biofilm covered surface where it is readily absorbed by the negative surfaces of proteins and bacteria. (Block, S, Disinfection, Sterilization & Preservation, Lea & Febiger, Phil., 1983). It thus serves as a binding agent between the dual quat and the application surface. This multi-purpose component helps create the unique aspect of the formulation.

The alcohol is preferably isopropyl alcohol. The use of isopropyl alcohol is involved as a solvent and aid in the disruptive mechanism of the biocidal formula by interaction with lipids and a denaturing action of proteins. Essentially, this is a reinforcement of the quats action along with the displacement of water molecules. This results in enzyme damage and conformational membrane changes resulting in cell leakage through membrane damage.

The surfactant is a third generation "Dual Quat" comprising an equal mixture of alkyl dimethyl benzyl ammonium chloride plus alkyl dimethyl ethylbenzyl ammonium chloride. This mixture of two specific quats results in a dual quat offering increased biocidal activity, stronger detergency, and increased safety to the user (relative lower toxicity). This synergistic additive functionally allows for the OPA to be more effective at all levels of concentration and at a stable temperature. One commercial example is distributed by Stepan, Inc. as BTC™ 2125 with a chain length distribution for the n-alkyl of about 60% $C_{14}$, about 30% $C_{16}$, about 5% $C_{12}$, and about 5% $C_{18}$. Besides acting as coadjuvant with the OPA, the dual-quat surfactant is and of itself biocidal and as such is interactive by itself versus an ineffective surfactant type alone.

It is the rapidly unexpected cidal effectiveness that is created by this unique and unusual combination of components that together work in a synergistic and additive manner to develop a new and unusual combination formula. The ability of the dual quaternary ammonium compounds to work in hard water and proteinaceous soil along with high detergency, low toxicity make it a key adjunct. The disruption of the cytoplasmic membrane due to the dual quat adsorption on the cell surface and membrane is the important factor.

The above-described formulation illustrates the improved kill, and improved kill time, all at normal 20 degrees C. Overall, the newly developed biologically designed chemical combination enhances biocidal effectiveness. This is accomplished by improving and opening the diffusion channels through the cell wall, leading to disruption of the cytoplasmic membrane. This is partly accomplished by adsorption of the cidal agent via the surfactant to the bacterial cell surface and cytoplasmic membrane.

It should now be apparent that the above-described improvement in aldehyde formulation results in a one step biocidal process requiring no activation, no dating (record-keeping) and is based upon biochemical principles that improves effectiveness. Toxicity is reduced, cidal effectiveness greatly improved, and no temperature control is required inasmuch as the formulation remains effective within federal standards at between 20-22 degrees C. Moreover, handlers are safer due lack of odor, low vapor pressure, reduced antigenic properties and improved waste disposal. The formulation may be considered a "green" formulation inasmuch as it is less toxic to the environment and ecosystem.

The above-described embodiment is especially well-suited for healthcare such as sterilizing medical instruments, and the following examples illustrate the efficacy in this context.

EXAMPLE 1

A formula of OPA—0.5%, Dual Quat—0.48%, and IPA—41% was applied to a challenge microorganism comprising *mycobacterium bovis* with an average cfu/carrier amount of $1.4 \times 10^5$—Acid fast stain confirmed *M. bovis*. Ten tubes were tested at 20 degrees C. for ten minutes and five minutes with an organic load of 5% in Kirchener medium. Test performed at 20° C. All passed at the 5 minute and 10 minute time and remained clear for 60 days.

EXAMPLE 2

The same formula concentration was used following AOAC guidelines against *Staph aureus, Ps. aeruginosa, S. choleraesuis, T. mentogrophytes*. 5% organic soil was added in synthetic broth. The carrier type used was stainless steel penicylinders. Test were performed at 20° degrees C. Ten carriers were exposed for 5 minutes. No carriers showed growth.

EXAMPLE 3

Sporicidal Sterility Test

Given formula concentration of OPA of 2%, dual chain quat 0.48%, and IPA of 42.0%, test was carried out using AOAC sporicidal guidelines. The challenge microorganisms were *Bacillus subtillus* and *Clostridium* sporogenes. Modified fluid thioglycollate medium was used. Temperature was 20 degrees C. Five carriers were tested of each organism. Exposure time was 10 hours. Incubation time was 21 days. Carriers were porcelain penicylinders and surgical threads. No growth was determined.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A biocidal formulation comprising orthophthalaldehyde and dual chain quaternary ammonium compound within the following acceptable ranges, isopropyl alcohol and water:
   orthophthalaldehyde 0.25% to 7% by total weight of the formulation;
   dual chain quaternary ammonium compound 0.24% to 6% by total weight of the formulation.

2. The biocidal formulation according to claim 1 wherein said dual chain quaternary ammonium compound consists of equal values of N-alkyl dimethylbenzyl ammonium chloride- and N-alkyl dimethylethylbenzyl ammonium chloride.

3. The biocidal formulation according to claim 1 wherein said isopropyl alcohol comprises a range of from 10.00%-60.00% by weight.

4. The biocidal formulation according to claim 1 comprising a pH within a range of from pH 3 to pH 9.

5. The biocidal formulation according to claim 1 for use as a sterilizing/high level disinfecting solution on immersed instruments within 10 hrs sterilization and 7 minutes disinfection.

6. The biocidal formulation according to claim 1 in aqueous form.

7. The biocidal formulation according to claim 1 in a spray format.

8. The biocidal formulation according to claim 1 in a wet wipe substrate.

9. The biocidal formulation according to claim 1 atomized within a pressurized pouch system.

* * * * *